United States Patent
Wu et al.

(10) Patent No.: US 12,285,284 B2
(45) Date of Patent: Apr. 29, 2025

(54) SYSTEMS AND METHODS FOR ARTIFACT REDUCTION IN TOMOSYNTHESIS WITH DEEP LEARNING IMAGE PROCESSING

(71) Applicant: The General Hospital Corporation, Boston, MA (US)

(72) Inventors: Dufan Wu, Boston, MA (US); Kyungsang Kim, Boston, MA (US); Quanzheng Li, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 411 days.

(21) Appl. No.: 17/759,737

(22) PCT Filed: Jan. 29, 2021

(86) PCT No.: PCT/US2021/015677
§ 371 (c)(1),
(2) Date: Jul. 29, 2022

(87) PCT Pub. No.: WO2021/155123
PCT Pub. Date: Aug. 5, 2021

(65) Prior Publication Data
US 2023/0110904 A1    Apr. 13, 2023

Related U.S. Application Data

(60) Provisional application No. 62/968,589, filed on Jan. 31, 2020.

(51) Int. Cl.
*G06K 9/00*     (2022.01)
*A61B 6/00*     (2006.01)
(Continued)

(52) U.S. Cl.
CPC ............. *A61B 6/502* (2013.01); *A61B 6/025* (2013.01); *A61B 6/5217* (2013.01);
(Continued)

(58) Field of Classification Search
CPC . G06T 11/003–008; G06T 2207/10112; G06T 2207/30068; G06T 2207/20081;
(Continued)

(56) References Cited

U.S. PATENT DOCUMENTS

2014/0294138 A1* 10/2014 Jerebko ................ A61B 6/025
378/4
2017/0071562 A1* 3/2017 Suzuki ................... G06T 5/00
(Continued)

FOREIGN PATENT DOCUMENTS

WO     2021155123 A1    8/2021

OTHER PUBLICATIONS

Hemant Kumar Aggarwal, Merry P. Mani, Mathews Jacob, "MoDL: Model Based Deep Learning Architecture for Inverse Problems", IEEE Transactions on Medical Imaging, vol. 38, No. 2, Feb. 2019, pp. 394-405 (Year: 2019).*

(Continued)

*Primary Examiner* — Atiba O Fitzpatrick
(74) *Attorney, Agent, or Firm* — QUARLES & BRADY LLP

(57) ABSTRACT

Systems and methods are provided for a deep learning-based digital breast tomosynthesis (DBT) image reconstruction that mitigates limited angular artifacts and improves in-depth resolution of the resulting images. The systems and methods may reduce the sparse-view artifacts in DBT via deep learning without losing image sharpness and contrast. A deep neural network may be trained in a way to reduce training-time computational cost. An ROI loss method may be used for further improvement on the resolution and contrast of the images.

23 Claims, 5 Drawing Sheets

(51) Int. Cl.
- *A61B 6/02* (2006.01)
- *A61B 6/50* (2024.01)
- *G06T 5/60* (2024.01)
- *G06T 5/70* (2024.01)
- *G06T 7/00* (2017.01)

(52) U.S. Cl.
CPC .............. *A61B 6/5258* (2013.01); *G06T 5/60* (2024.01); *G06T 5/70* (2024.01); *G06T 7/0012* (2013.01); *G06T 2207/10116* (2013.01); *G06T 2207/20081* (2013.01); *G06T 2207/20084* (2013.01); *G06T 2207/30068* (2013.01)

(58) Field of Classification Search
CPC . G06T 2207/20084; G06T 9/002; G06T 5/60; G06T 2211/436; G06T 2207/30096; A61B 6/025; A61B 6/502; A61B 6/5258–5282; A61B 6/583; A61B 6/584; G06K 9/6256; G06K 9/6257; G06K 9/6259; G06V 10/70; G06V 10/82; G06V 10/774–7796; G06V 10/454; G06V 2201/032; G06N 3/02–126; G06N 20/00–20; G06F 18/214–2155; G06F 7/023; G06F 40/16; G01N 29/4481
See application file for complete search history.

(56) References Cited

U.S. PATENT DOCUMENTS

| | | | |
|---|---|---|---|
| 2019/0102916 A1* | 4/2019 | Palma | G06N 3/08 |
| 2019/0147588 A1 | 5/2019 | Rowley Grant et al. | |
| 2019/0251713 A1* | 8/2019 | Chen | A61B 6/482 |
| 2019/0325621 A1 | 10/2019 | Wang et al. | |
| 2020/0196973 A1* | 6/2020 | Zhou | G06N 3/045 |
| 2020/0211240 A1* | 7/2020 | Bernard | G06T 11/008 |
| 2020/0289019 A1* | 9/2020 | Schlemper | G06T 3/60 |
| 2021/0279847 A1* | 9/2021 | Nett | G06T 11/008 |
| 2024/0119586 A1* | 4/2024 | Natarajan | G16H 50/70 |

OTHER PUBLICATIONS

Dufan Wu, Kyungsang Kim, and Quanzheng Li, "Computationally Efficient Cascaded Training for Deep Unrolled Network in CT Imaging", Oct. 5, 2018 (Year: 2018).*
Adler et al., "Learned Primal-Dual Reconstruction," IEEE Transactions on Medical Imaging, vol. 37, No. 6, pp. 1322-1332, (2018).
Bakic et al., "Development and chacterization of an anthropomophic breast software phantom based upon region-growing algorithm," Medical Physics, vol. 38, No. 6, Part 1, pp. 3165-3176, May 2011.
DeSantis, C.E., et al., 2017. Breast cancer statistics, 2017, racial disparity in mortality by state. CA: a cancer journal for clinicians, 67(6), pp. 439-448.
Elbakri et al., "Statistical image reconstruction for polyenergetic X-ray computed tomography," IEEE transactions on medical imaging, vol. 21, No. 2, pp. 89-99, Feb. 2002.
Erickson, David W., et al. "Population of 224 realistic human subject-based computational breast phantoms." Medical physics 43.1 (2016): 23-32.
Gur et al., "Digital breast tomosynthesis: Observer performance study," American Journal of Roentgenology, vol. 193, No. 2, pp. 568-591, Aug. 2009.
International Search Report and Written Opinion issued in corresponding PCT Application No. US2021/015677, issued Apr. 26, 2021.
Kim et al., "Fully iterative scatter corrected digital breast tomosynthesis using GPU-based fast Monte Carlo simulation and composition ratio update," Medical Physics, vol. 42, No. 9, pp. 5342-5355, Aug. 2015.
Michielsen, et al., "Deep Learning-based Initialization of Iterative Reconstruction for Breast Tomosynthesis", The 6th International Conference on Image Formation in X-Ray Computed Tomography, (2020).
Moriakov et al., "Deep Learning Framework for Digital Breast Tomosynthesis Reconstruction", arXiv:1808.04640v1 [physics.med-ph] Aug. 14, 2018.
Parikh, "Proximal Algorithms," Foundations and Trends® in Optimization, vol. 1, No. 3, pp. 127-239, 2014.
Wu et al., "Computationally Efficient Deep Neural Network for Computed Tomography Image Reconstruction," In: Cornell University Library/ Computer Science/Computer Vision and Pattern Recognition, May 24, 2019.
Wu et al., (2020). "Digital Breast Tomosynthesis Reconstruction with Deep Neural Network for Improved Contrast and In-Depth Resolution." 656-659. 10.1109/ISBI45749.2020.9098661.

* cited by examiner

SYSTEMS AND METHODS FOR ARTIFACT REDUCTION IN TOMOSYNTHESIS WITH DEEP LEARNING IMAGE PROCESSING

CROSS-REFERENCE TO RELATED APPLICATIONS

This application represents the U.S. national stage entry of PCT International Application No. PCT/US2021/015677 filed Jan. 29, 2021, which claims the benefit of U.S. Provisional Patent Application Ser. No. 62/968,589 filed on Jan. 31, 2020 and entitled "System and Method of Sparse-View Artifacts Reduction in Digital Breast Tomosynthesis with Deep-Learning-Based Image Processing," the contents of each are incorporated herein by reference as if set forth in its entirety for all purposes.

STATEMENT REGARDING FEDERALLY SPONSORED RESEARCH

N/A

BACKGROUND

Breast cancer is the second most common cancer in women. It is also the second leading cause of cancer death among American women. Evidence has shown that screening and early detection is the key to prevent breast cancer death. Screening is conventionally performed using mammography, which provides for 2D imaging, but the breast tissue depicted may be overlapping due to a single view angle. Digital breast tomosynthesis (DBT) is an emerging, promising new technology for breast cancer screening imaging that takes several images from different angles, which may be from different depths that may be stacked to form a 3D image. Compared to the conventional X-ray mammography, DBT has significantly improved sensitivity and specificity. Meanwhile, DBT has very similar hardware setup with mammography, which lowers the cost for both manufacturers and users to upgrade from mammography to DBT.

Digital breast tomosynthesis (DBT) provides 3D reconstruction which reduces the superposition and overlapping of breast tissues compared to mammography, leading to increased sensitivity and specificity. However, to save dose and scanning time, most DBT system has large sampling interval ($\leq 3°$) and a very limited angular sampling range of 50°. The large angular interval leads to sparse-view artifacts, where streaks due to high-contrast objects are visible in the DBT images. The artifacts cause ambiguity in some cases when they are overlapping with local structures. The obvious artifacts also lowered physician's confidence when making decision with the DBT images. DBT images also may suffer from limited in-depth resolution.

3D DBT also has very high resolution, which leads to huge training computational cost. Thus, there remains a need for a DBT reconstruction method to mitigate the limited angular artifacts and improve in-depth resolution while avoiding computational cost burdens.

SUMMARY OF THE DISCLOSURE

The present disclosure addresses the aforementioned drawbacks by providing systems and methods for a deep learning-based tomosynthesis reconstruction that mitigates the limited angular artifacts and improves in-depth resolution. The systems and methods can reduce the sparse-view artifacts in DBT via deep learning without clinically damaging image sharpness and contrast. A deep neural network may be trained, such as an unroll-type neural network, and may be used with a decoupled training for each unroll to reduce training-time computational cost.

In one configuration, a method is provided for artifact reduction in tomosynthesis imaging of a subject. The method includes accessing a decoupled trained, unroll-type neural network trained to suppress artifacts using decoupled training with image training data that include at least one artifact. The method also includes accessing tomosynthesis image data of the subject that includes a region of interest (ROI) and subjecting the tomosynthesis image data to the decoupled trained unroll-type neural network to reconstruct an image of the subject with suppressed artifacts in the region of interest. The method also includes displaying the image of the subject with suppressed artifacts.

In one configuration, a system is provided for artifact reduction in tomosynthesis imaging of a subject. The system includes a computer system configured to access a decouple trained, unroll-type neural network trained to suppress artifacts using decoupled training with image training data that include at least one artifact. The computer system is also configured to access tomosynthesis image data of the subject that includes a region of interest and subject the tomosynthesis image data to the decoupled trained unroll-type neural network to reconstruct an image of the subject with suppressed artifacts in the region of interest. The computer system is also configured to display the image of the subject with the suppressed artifacts.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention. Like reference numerals will be used to refer to like parts from Figure to Figure in the following description.

DETAILED DESCRIPTION

Systems and methods are provided for a deep learning-based tomosynthesis image reconstruction, such as a digital breast tomosynthesis (DBT) image reconstruction, that mitigates limited angular artifacts and improves in-depth resolution of the resulting images. The systems and methods may reduce the sparse-view artifacts in DBT via deep learning without losing image sharpness and contrast. A deep neural network may be trained, such as an unroll-type neural network, and may be used with a decoupled training for each unroll to reduce training-time computational cost. In some configurations, an ROI loss may be used for further improvement on the resolution and contrast of the images.

In some configurations, a region of interest loss method on microcalcifications may be used to improve the spatial resolution and contrast of the regions of interest, such as on microcalcifications. In a non-limiting example, the network was trained and tested on 176 realistic breast phantoms, and demonstrated improved in-plane contrast (3.17 versus 0.43, p<0.01) and in-depth resolution (1.19 mm versus 4.96 mm, p<0.01) as compared to an iterative reconstruction (IR) method.

Figure 1:
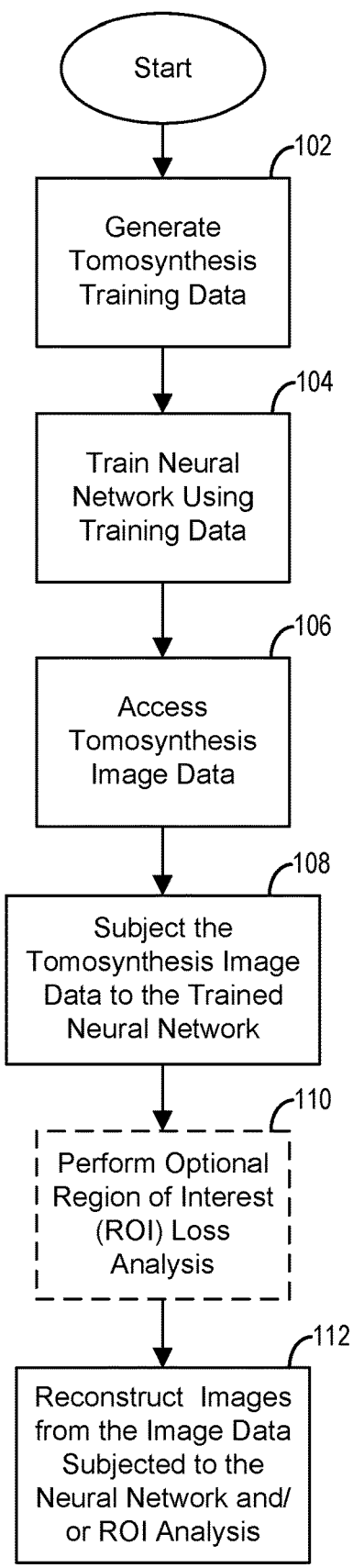
FIG. 1 is a flow chart of non-limiting example steps for a method of tomosynthesis image reconstruction in accordance with the present disclosure.

Referring to FIG. 1, a flow chart of non-limiting example steps for a method of tomosynthesis image reconstruction is shown. Tomosynthesis training data may be generated at step 102. A neural network may be trained using the training data at step 104. The resulting, trained neural network may be stored and accessed for later use.

When images of a particular subject are needed, tomosynthesis image data of the subject may be accessed or otherwise acquired at step 106. Tomosynthesis image data may include digital breast tomosynthesis image data. Then, the trained neural network can be accessed and the tomosynthesis image data is subjected to the trained neural network at step 108. An optional region of interest loss analysis may be performed on the tomosynthesis image data at step 110. Images of the subject may be reconstructed from the image data that was subjected to the neural network and/or the ROI loss analysis to thereby produce, as will be described, images with suppressed artifacts.

Training of a neural network may include using realistic breast phantoms or real patients' data. Numerical breast phantoms are a reliable choice for DBT simulation because of the extensive existing studies that have proven the performance of these phantoms. Real patients' data may yet be more precise in some aspects. When training a neural network, both dense-view sampling (e.g. 0.5°) and sparse-view sampling may be acquired from the scans. In some configurations, the ROIs may be annotated, such as by a human annotator. These ROIs may contain the sparse-view artifacts in the sparse-view reconstruction results. A deep neural network with an ROI loss may be trained to suppress the artifacts while keeping existing structures.

In one configuration, a neural network is an unrolled network, which may solve the following optimization problem:

$$x^* = \mathrm{argmin}_x \|Ax - b\|_w^2 + \beta R(x) \quad (1)$$

where x is the image to be reconstructed, A is the system matrix, b is the projection data, w is the noise weighting matrix, R(x) is the prior function, and p is the hyperparameter to balance between data fidelity and the prior knowledge.

Equation (1) can be solved via proximal gradient descent:

$$x^n = \mathrm{prox}_{\gamma\beta R}\{x^{(n-1)} - \gamma A^T w (A x^{n-1}) - b)\} \quad (2)$$

where γ is a suitable step size for the gradient descent. The decoupled unrolled network may replace proximal mapping with CNNs and the gradient descent step with separable quadratic surrogate (SQS). The SQS is free of choosing step size γ and has faster convergence. The SQS step may be noted as:

$$g(x) = x - \frac{A^T w(Ax - b)}{A^T A 1} \quad (3)$$

The decoupled unrolled network can be expressed as:

$$x^{(n)} = f(g^M(x^{(n-1)}), x^{(n-1)}; \Theta^{(n)}) \quad (4)$$

where f(y, x; $\Theta^{(n)}$) is a CNN with trainable parameters $\Theta^{(n)}$ and input y and x concatenated along the channel direction. $g^M (x^{n-1})$ means Mth iterations of SQS (3) being applied to input image $x^{(n-1)}$. The network was trained sequentially from the first unroll to the last unroll. The training at nth unroll may be expressed as:

$$\Theta^{(n)} = \mathrm{argmin}_\Theta \sum \|f(g^M(x_i^{(n-1)}), x_i^{(n-1)}; \Theta) - x_i^{ref}\| \quad (5)$$

where $x_i^{ref}$ is the label image of the ith training sample, and $x_i^{n-1}$ is the output of trained networks for the ith sample. Compared to most unrolled networks which need simultaneously optimization of $\Theta^{(1)}$ to $\Theta^{(N)}$, the decoupled training may only be optimized one OM at a time. That is, conventional training techniques suffer from large memory consumption issues when processing 3D volume data, whereas decoupled unrolled network training may train each iteration step separately to reduce memory costs. The feature map size may be significantly reduced, leading to less training memory and time requirement.

Figure 2:
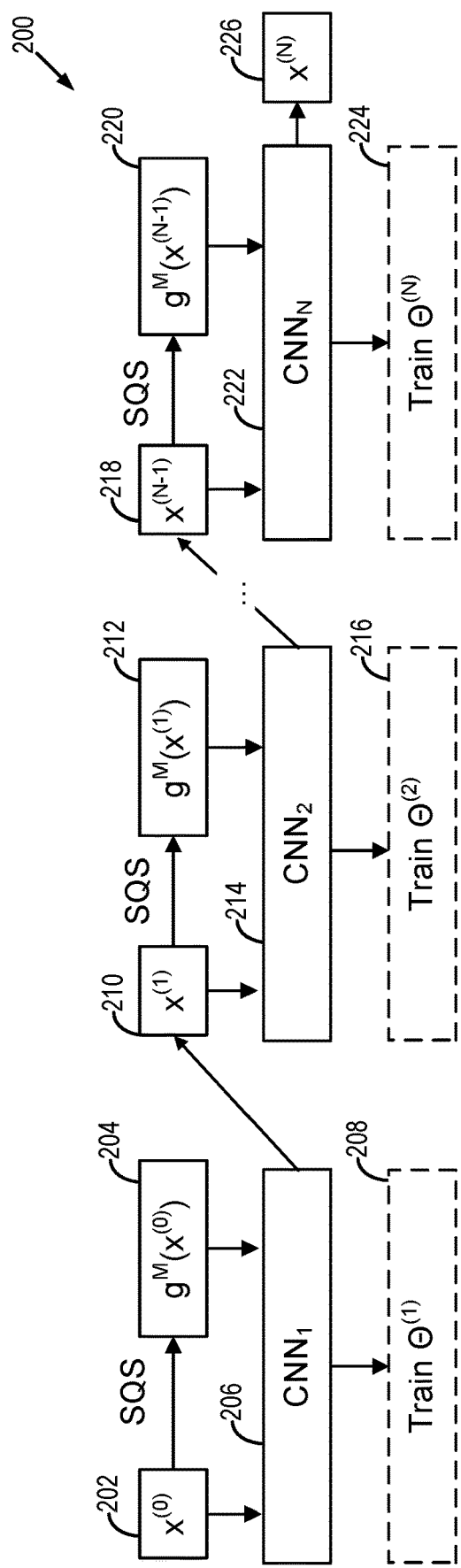
FIG. 2 is a non-limiting example convolutional neural network (CNN) architecture that may be used in accordance with the present disclosure.

Referring to FIG. 2, a non-limiting example convolutional neural network architecture in accordance with the present disclosure is shown. The convolutional neural network is shown as a decoupled unrolled network 200. The decoupled unrolled network 200 includes initial input 202, initial separable quadratic surrogate 204, first convolutional neural network level 206, and initial training data 208. The decoupled unrolled network 200 also includes a subsequent input 210, a subsequent separable quadratic surrogate 212, a subsequent convolutional neural network level 214, and subsequent training data 216. This framework extends such that the decoupled unrolled network 200 also includes N−1 input 218, N−1 separable quadratic surrogate 220, N convolutional neural network level 222 and N training data 224. The result from the decoupled unrolled network 200 is delivered via output 226.

Non-Limiting Example Region of Interest Loss

Detection of microcalcification is one non-limiting example application of DBT. Microcalcifications could be early signs of breast cancer, and they usually have diameter of several hundred micrometers and significantly higher density compared to breast tissues. Because microcalcifications are extremely small compared to the whole volume, they may provide limited contributions to the training loss and may be ignored by the network during training in some cases. The microcalcifications may be significantly different from the other breast tissues that a network was trained on, which may led to limited contrast and in-depth resolution improvement of microcalcifications compared to iterative reconstructions. In accordance with the present disclosure, these limitations may be addressed by including the ROI loss in addition to the whole-volume L2 loss. In some configurations, this may be reflected as:

$$\Theta^{(n)} = \underset{\Theta}{\operatorname{argmin}} \sum \frac{1}{J} \left\| f_i^{(n-1)}(\Theta) - x_i^{ref} \right\|_2^2 + \lambda \sum_i \sum_{k=1}^{K_i} \frac{1}{J_r K_i} \left\| E_{ik} \left( f_i^{(n-1)}(\Theta) - x_i^{ref} \right) \right\|_2^2 \quad (6)$$

where J is the total number of voxels of an image; Jr is the total number of voxels of ROIs; K, is the number of ROIs of sample i; $E_{ik}$ is the masking matrix for ROI k in sample i; λ is a hyperparameter to balance between whole-image loss and ROI loss $f_i^{(n-1)}(\Theta)=f(g^M(x_i^{(n-1)}),x_i^{(n-1)};\Theta)$ as in equation (5).

Non-Limiting Example Breast Phantom Application

In a non-limiting example, a dataset consisted of 176 realistic breast phantoms derived from breast CT scans of healthy subjects. Each breast CT image was segmented into six classes including skin, adipose, glandular and 3 different mixtures of adipose and glandular. Finite element model was applied to the segmented images to simulate breast compression between 50 to 80 mm. We assigned μ=0.456 $cm^{-1}$ for adipose and μ=0.802 $cm^{-1}$ for glandular and skin. For faster computation, the voxel size was downsampled from 0.25×0.25×0.25 $mm^3$ to 1×1×1 $mm^3$. The downsampling did not interfere with the limited angular artifacts, because the artifacts mostly exists in low frequency.

Calcification points were further inserted into phantoms with μ from 1.011 $cm^{-1}$ to 3.034 $cm^{-1}$, which was corresponding to 10% to 30% of the attenuation coefficient of calcium oxalate at 20 keV. Each calcification point only occupied one single voxel and each patient was randomly assigned 0 to 4 calcification points. The 10% to 30% scale factor was corresponding microcalcifications' diameter of 0.1 mm to 0.3 mm whereas our voxel size was 1 mm.

A detector with pixel size of 0.5×0.5 $mm^2$ was used. The projecting geometry was configured where the source to detector distance was 660 mm, source to rotation center distance was 627 mm and the breast was placed 10 mm above the detector surface. The angular sampling was from −21° to +21° with 3° interval, giving 15 views in total. Distance driven projector and backprojector were used for both simulation and reconstruction. Poisson noise was added to the projections assuming $10^5$ initial photons per ray.

In the non-limiting example, 140 patients were randomly selected for training whereas the remaining 36 patients were used for testing. UNet with depth of 4 was used as the CNN in each unroll. An unroll number N=10 and SQS iterations M=10 were used. The initial image $x^{(0)}$ was 10 SQS iterations from zero images. Each unroll was trained by Adam optimizer with learning rate of $10^{-3}$ for 150 epochs. The entire training took approximately 12 hours. For the ROI loss, 9×9×9 ROIs were selected around each inserted calcification point with λ set to 0.1. IR results from 20 iterations of SQS from zero were used for comparison. The number of iterations balanced between noise level and artifacts. The thicknesses of the breast were assumed to be known for both IR and deep learning to further reduce limited angular artifacts. Thickness can be measured by the compressor of DBT scanners.

Deep learning results gave significantly improved contrast for in-plane structures with less superposition. In the non-limiting example, both axial and sagittal views showed a structure where deep learning achieved improved in-plane contrast and better in-depth resolution compared to IR. A calcification point was also zoomed in, and deep learning with ROI loss demonstrated significantly improved contrast compared to IR and L2 loss. In addition, there were obvious wave-like artifacts in the IR result which was caused by the sparse sampling. These artifacts were not present in the deep learning results.

Root mean square errors (RMSE) and structural similarity indices (SSIM) were calculated for each testing images comparing to the ground truth. Both deep learning-based results had significantly improved metrics compared to IR (p<0.01). Furthermore, ROI loss only led to slightly worse overall RMSEs and SSIMs compared to L2 loss. There was no substantial visual difference of the glandular reconstructed using the two losses in FIG. 2.

The contrast and spatial resolution were quantitatively analyzed at the calcification points. For each point, a Gaussian function was used to fit the profile along x, y and z directions in a 21-pixel window. The in-depth resolution was calculated as the full width at half maximum (FWHM) of the Gaussian function along z, and the in-plane resolution was taken as the average of FWHM along x and y direction. The Weber contrast was determined, which may be defined as $$c = \frac{I_{peak} - I_{background}}{I_{background}} \quad (7)$$

where Ipeak is the peak intensity as the peak of the Gaussian function, and Ibackground is the background intensity as the bias of the Gaussian function. ROI loss significantly improved resolution and contrast over L2 loss and IR (p<0.01).

In a non-limiting example, downsampled phantoms were used, but the network may be scaled to larger volumes in applications without additional requirement on computational hardware. The trained networks may also be applied to real DBT data. In a non-limiting example, the trained network was further applied to real DBT data from 15 patients and demonstrated improved in-plane contrast and in-depth resolution. In one of the 15 patients, the upper and lower borders of a concentrated mass can be identified in the network results, which was otherwise indistinguishable in the IR results.

Figure 3:
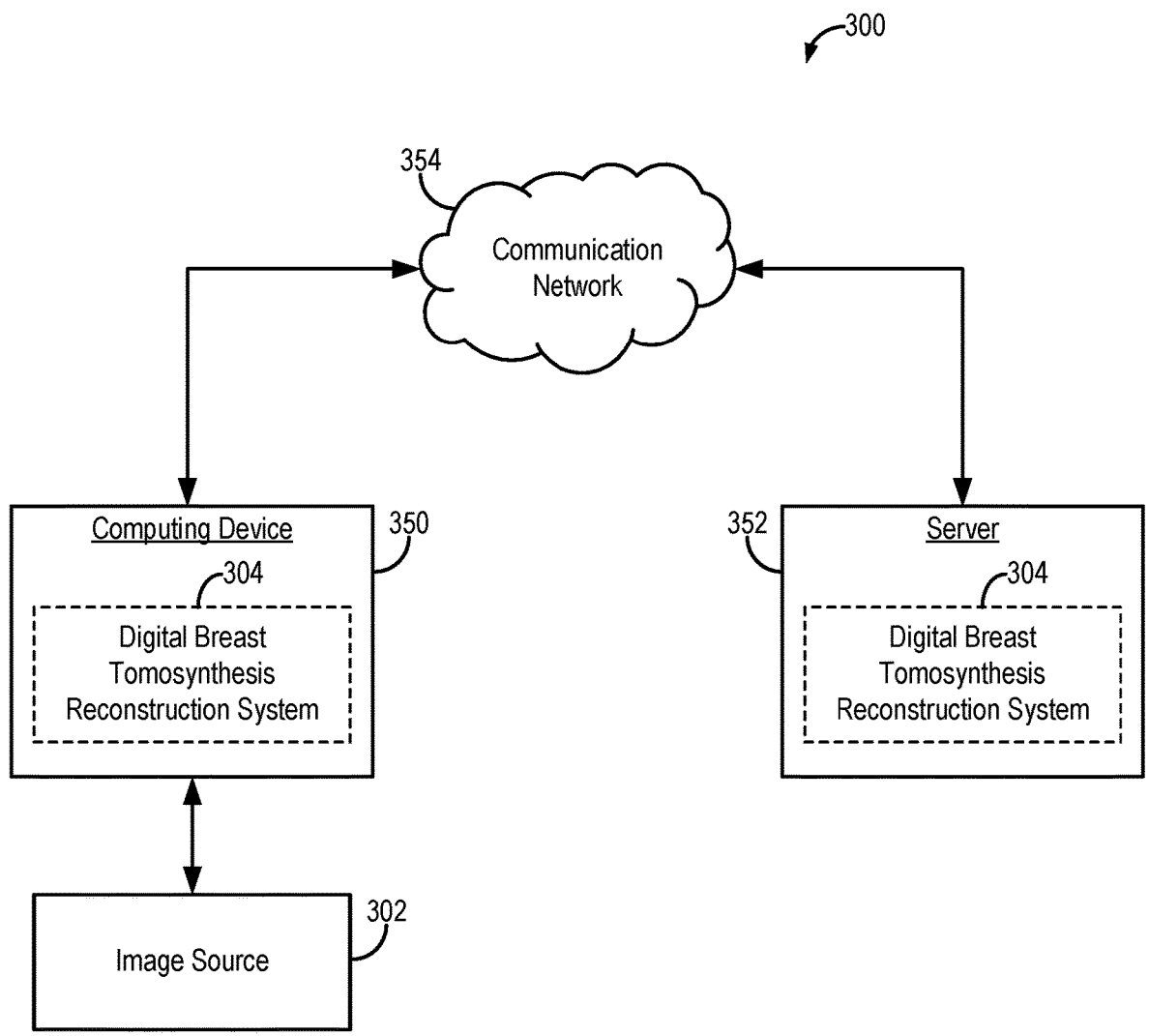
FIG. 3 is a block diagram of an example system that can implement a digital breast tomosynthesis reconstruction system for generating images of a subject using a machine learning or deep learning method.

Referring to FIG. 3, an example of a system 300 for generating and implementing a machine learning or deep learning routine in accordance with some embodiments of the systems and methods described in the present disclosure is shown. As shown in FIG. 3, a computing device 350 can receive one or more types of data (e.g., digital breast tomography, x-ray, computed tomography, ultrasound, multiparametric MRI data, breast image data, and the like) from image source 302. In some embodiments, computing device 350 can execute at least a portion of a digital breast tomosynthesis reconstruction system 304 to generate images of a breast, or otherwise segment a region of interest from data received from the image source 302.

Additionally or alternatively, in some embodiments, the computing device 350 can communicate information about data received from the image source 302 to a server 352 over a communication network 354, which can execute at least a portion of the digital breast tomosynthesis reconstruction system 304 to generate images of a region of interest, or otherwise segment a region of interest from data received from the image source 302. In such embodiments, the server 352 can return information to the computing device 350 (and/or any other suitable computing device) indicative of an output of the digital breast tomosynthesis reconstruction system 304 to generate images of a region of interest, or otherwise segment a region of interest from data received from the image source 302.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, image source 302 can be any suitable source of image data (e.g., measurement data, images reconstructed from measurement data), such as a digital breast tomosynthesis system, another computing device (e.g., a server storing image data), and so on. In some embodiments, image source 302 can be local to computing device 350. For example, image source 302 can be incorporated with computing device 350 (e.g., computing device 350 can be configured as part of a device for capturing, scanning, and/or storing images). As another example, image source 302 can be connected to computing device 350 by a cable, a direct wireless link, and so on. Additionally or alternatively, in some embodiments, image source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
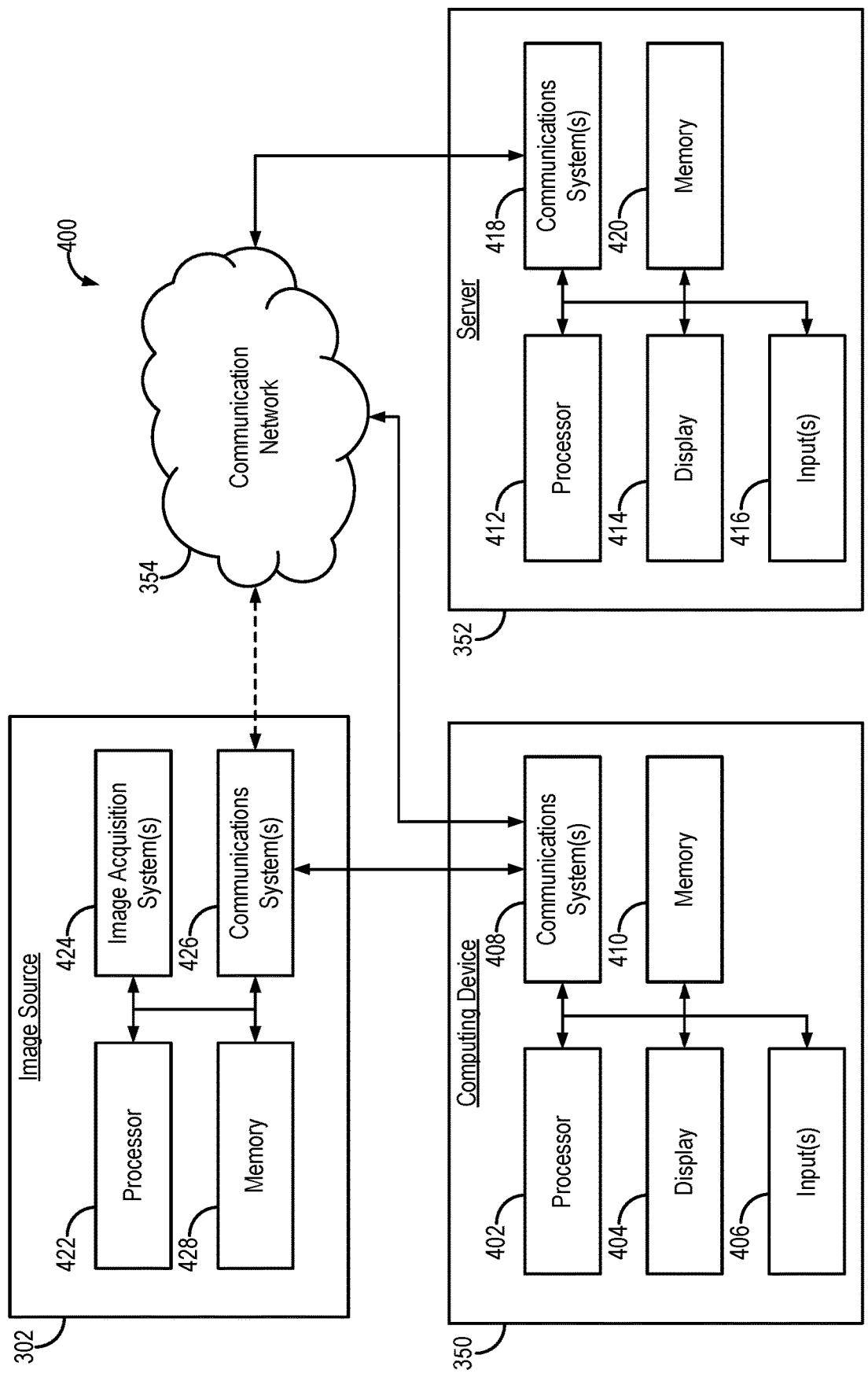
FIG. 4 is a block diagram of example hardware components of the system of FIG. 3.

Referring now to FIG. 4, an example of hardware 400 that can be used to implement image source 302, computing device 350, and server 354 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a Wi-Fi connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, image source 302 can include a processor 422, one or more image acquisition systems 424, one or more communications systems 426, and/or memory 428. In some embodiments, processor 422 can be any suitable hardware processor or combination of processors, such as a CPU, a GPU, and so on. In some embodiments, the one or more image acquisition systems 424 are generally configured to acquire data, images, or both, and can include an RF transmission and reception subsystem of a digital breast tomosynthesis system. Additionally or alternatively, in some embodiments, one or more image acquisition systems 424 can include any suitable hardware, firmware, and/or software for coupling to and/or controlling operations of an digital breast tomosynthesis system. In some embodiments, one or more portions of the one or more image acquisition systems 424 can be removable and/or replaceable.

Note that, although not shown, image source 302 can include any suitable inputs and/or outputs. For example, image source 302 can include input devices and/or sensors that can be used to receive user input, such as a keyboard, a mouse, a touchscreen, a microphone, a trackpad, a trackball, and so on. As another example, image source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more image acquisition systems 424, and/or receive data from the one or more image acquisition systems 424; to images from data; present content (e.g., images, a user interface) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of image source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 5:
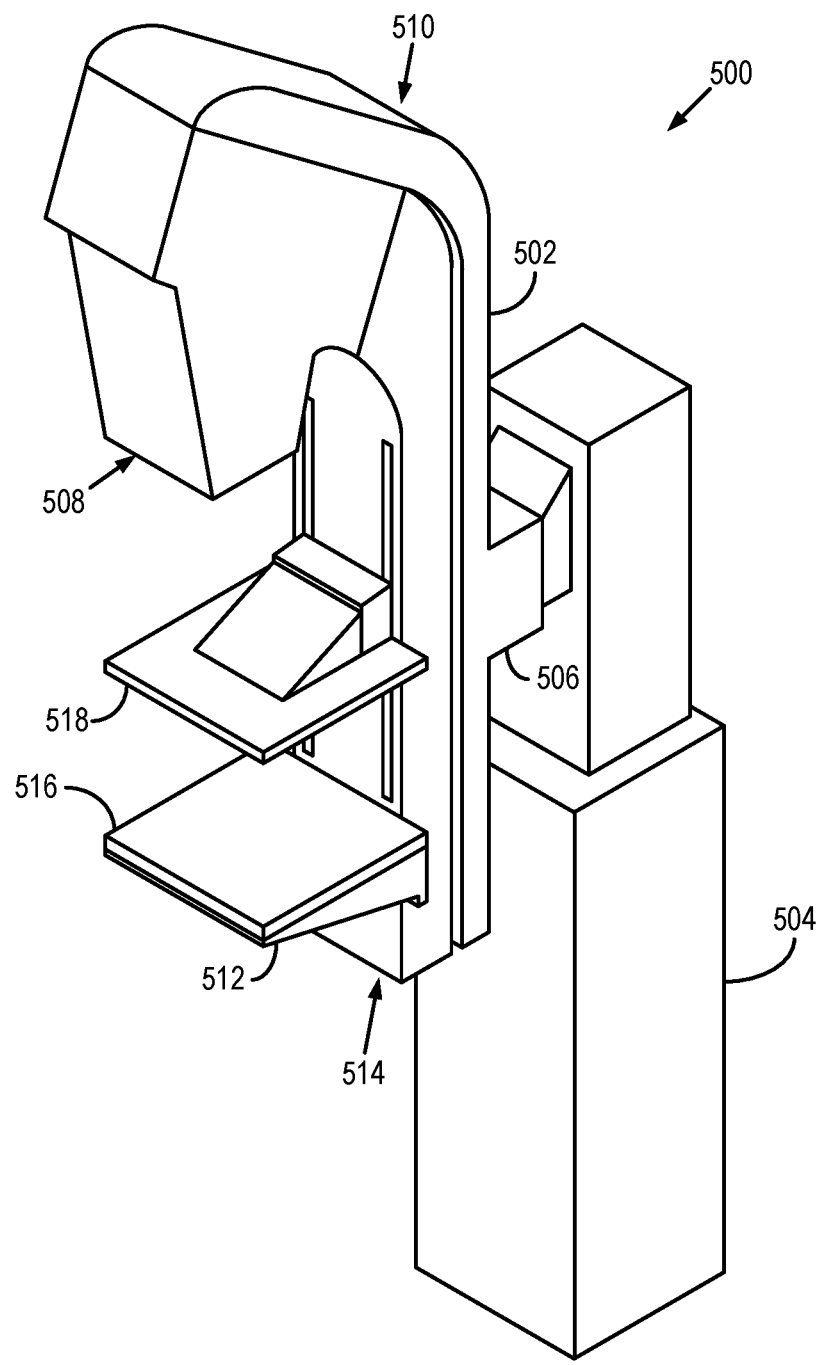
FIG. 5 is a block diagram of a non-limiting example digital breast tomosynthesis (DBT) system.

Referring to FIG. 5, a non-limiting example digital breast tomosynthesis (DBT) system 500 is shown that may be used in accordance with the present disclosure. DBT system 500 may include a drive plate 518 configured to provide compression against a compression plate 516 for an organ disposed between drive plate 518 and compression plate 516. Imaging detectors 512 may be coupled to a mounting system 514. Radiation source 508 may be coupled to support system 502 and coupled to base 504 with rotatable coupler 506.

The present disclosure has described one or more preferred embodiments, and it should be appreciated that many equivalents, alternatives, variations, and modifications, aside from those expressly stated, are possible and within the scope of the invention.

The invention claimed is:

1. A method for artifact reduction in tomosynthesis imaging of a subject, the method comprising:
    a) accessing a decoupled trained, unroll-type neural network trained to suppress at least sparse-view artifacts using decoupled training with image training data that include at least one sparse-view artifact;
    b) accessing tomosynthesis image data of the subject that includes a region of interest;
    c) subjecting the tomosynthesis image data to the decoupled trained unroll-type neural network to reconstruct an image of the subject with suppressed sparse-view artifacts in the region of interest;
    d) displaying the image of the subject with the suppressed sparse-view artifacts.

2. The method of claim 1, wherein decoupled training includes optimizing one training parameter at a time.

3. The method of claim 2, wherein the decoupled trained unroll-type neural network is a convolutional neural network (CNN) with separable quadratic surrogate.

4. The method of claim 3, wherein the tomosynthesis image data is subjected to the decoupled trained unroll-type neural network over a plurality of iterations.

5. The method of claim 1, wherein the unroll-type neural network is trained sequentially from a first unroll to a last unroll.

6. The method of claim 5, wherein the image training data include dense-view sampling data and sparse-view sampling data.

7. The method of claim 6, wherein the sparse-view sampling data includes sparse-view artifacts, and wherein the at least one artifact included with the image training data is the sparse-view artifact.

8. The method of claim 1, wherein the tomosynthesis image data includes digital breast tomosynthesis image data.

9. The method of claim 8, wherein the digital breast tomosynthesis image data includes microcalcifications.

10. The method of claim 1, further comprising performing a region of interest loss analysis that applies a region-of-interest loss.

11. The method of claim 1, wherein the image training data includes image data of realistic numerical breast phantoms generated from data acquired with at least one of digital breast tomosynthesis, mammography, computed tomography (CT), breast CT, magnetic resonance (MR) or breast MR.

12. A system for artifact reduction in tomosynthesis imaging of a subject, the system comprising:
a computer system configured to:
i) access a decoupled trained, unroll-type neural network trained to suppress at least sparse-view artifacts using decoupled training with image training data that include at least one sparse-view artifact;
ii) access tomosynthesis image data of the subject that includes a region of interest;
iii) subject the tomosynthesis image data to the decoupled trained unroll-type neural network to reconstruct an image of the subject with suppressed sparse-view artifacts in the region of interest;
iv) display the image of the subject with the suppressed sparse-view artifacts.

13. The system of claim 12, wherein the computer system is further configured to decoupled train the unroll-type neural network by optimizing one training parameter at a time.

14. The system of claim 13, wherein the decoupled trained unroll-type neural network is a convolutional neural network (CNN) with separable quadratic surrogate.

15. The system of claim 14, wherein the computer system is further configured to subject the tomosynthesis image data to the decoupled trained unroll-type neural network over a plurality of iterations.

16. The system of claim 12, wherein the computer system is further configured to train the unroll-type neural network sequentially from a first unroll to a last unroll.

17. The system of claim 16, wherein the image training data include dense-view sampling data and sparse-view sampling data.

18. The system of claim 17, wherein the sparse-view sampling data includes sparse-view artifacts, and wherein the at least one artifact included with the image training data is the sparse-view artifact.

19. The system of claim 12, wherein the tomosynthesis image data includes digital breast tomosynthesis image data.

20. The system of claim 19, wherein the digital breast tomosynthesis image data includes microcalcifications.

21. The system of claim 12, wherein the computer system is further configured to perform a region of interest loss analysis.

22. The system of claim 21, wherein the region of interest loss analysis applies a region of interest loss that is separate from a whole-volume L2 loss applied by the decoupled trained unroll-type neural network.

23. The method of claim 12, wherein the image training data includes image data of realistic numerical breast phantoms generated from data acquired with at least one of digital breast tomosynthesis, mammography, computed tomography (CT), breast CT, magnetic resonance (MR) or breast MR.

* * * * *